(12) United States Patent
Lombardo

(10) Patent No.: US 6,238,396 B1
(45) Date of Patent: May 29, 2001

(54) SURGICAL CROSS-CONNECTING APPARATUS AND RELATED METHODS

(75) Inventor: Alan Lombardo, Kinnelon, NJ (US)

(73) Assignee: Blackstone Medical, Inc., Springfield, MA (US)

( * ) Notice: Subject to any disclaimer, the term of this patent is extended or adjusted under 35 U.S.C. 154(b) by 0 days.

(21) Appl. No.: 09/414,357

(22) Filed: Oct. 7, 1999

(51) Int. Cl.⁷ .................................................. A61B 17/70
(52) U.S. Cl. ............................................................ 606/61
(58) Field of Search .............................. 606/61, 60, 71, 606/59, 54, 53

(56) References Cited

U.S. PATENT DOCUMENTS

| | | |
|---|---|---|
| 4,085,744 | 4/1978 | Lewis et al. . |
| 4,641,636 | 2/1987 | Cotrel . |
| 4,815,453 | 3/1989 | Cortel . |
| 4,957,496 * | 9/1990 | Schmidt ............................. 606/71 X |
| 5,005,562 | 4/1991 | Cotrel . |
| 5,242,445 | 9/1993 | Ashman . |
| 5,282,801 | 2/1994 | Sherman . |
| 5,304,179 | 4/1994 | Wagner . |
| 5,334,203 | 8/1994 | Wagner . |
| 5,380,325 * | 1/1995 | Lahille et al. ......................... 606/61 |
| 5,437,669 | 8/1995 | Yuan et al. . |
| 5,507,747 * | 4/1996 | Yuan et al. ............................. 606/61 |
| 5,531,747 * | 7/1996 | Ray ....................................... 606/61 |
| 5,584,831 | 12/1996 | McKay . |
| 5,643,264 | 7/1997 | Sherman et al. . |
| 5,645,544 | 7/1997 | Tai et al. . |
| 5,667,507 | 9/1997 | Corin et al. . |
| 5,667,508 | 9/1997 | Errico et al. . |
| 5,688,272 | 11/1997 | Montague et al. . |
| 5,707,372 * | 1/1998 | Errico et al. ...................... 606/60 X |
| 5,709,684 * | 1/1998 | Errico et al. ........................... 606/61 |
| 5,716,355 | 2/1998 | Jackson et al. . |
| 5,752,957 | 5/1998 | Ralph et al. . |
| 5,810,818 | 9/1998 | Errico et al. . |
| 5,947,966 | 9/1999 | Drewry et al. . |
| 5,964,762 * | 10/1999 | Biedermann et al. ............. 606/61 X |
| 5,980,523 * | 11/1999 | Jackson ................................. 606/61 |
| 6,096,039 * | 8/2000 | Stoltenberg et al. ................... 606/61 |

FOREIGN PATENT DOCUMENTS

| | | | |
|---|---|---|---|
| 611116 * | 8/1994 | (EP) ...................................... 606/61 |
| 625337 * | 11/1994 | (EP) ...................................... 606/61 |
| 2704137 * | 10/1994 | (FR) ...................................... 606/61 |
| 1823791 * | 6/1993 | (SU) ...................................... 606/61 |

* cited by examiner

Primary Examiner—Jeffrey A. Smith
(74) Attorney, Agent, or Firm—Dreier & Baritz LLP.

(57) ABSTRACT

A surgical cross-connecting apparatus includes a first element, a second element, an adjustable tightening device and at least two rotatable hooking elements. The first element has opposing ends; one end has at least one aperture and the other end has a recessed surface including a central bore. The second element has opposing ends; one end having at least one aperture and the other end has a recessed surface including an elongated aperture. The recessed surface of the second element is positioned to overlap the recessed surface of the first element. The adjustable tightening device is positioned through the elongated aperture of the second element and within the central bore of the first element to secure the second element onto the first element. The tightening device is designed to rotatably fit and slidably move within the elongated aperture of the second element. The rotatable hooking elements comprises a hook and an adjustable securing device, and the hooking elements are inserted within the aperture of the first and second element.

40 Claims, 13 Drawing Sheets

SURGICAL CROSS-CONNECTING APPARATUS AND RELATED METHODS

BACKGROUND OF THE INVENTION

The present invention relates to a surgical cross-connecting apparatus and a cross-connecting surgical screw apparatus for use with implantation rods, and related methods of securing implantation rods using a surgical cross-connecting apparatus.

The bones and connective tissue of an adult human spinal column consists of more than 20 discrete bones coupled sequentially to one another by a tri-joint complex. The complex consists of an anterior disc and two posterior facet joints. The anterior discs of adjacent bones are cushioned by cartilage spacers referred to as intervertebral discs. The over 20 bones of the spinal column are anatomically categorized as one of four classification: cervical, thoracic, lumbar, or sacral. The cervical portion of the spine which comprises the top of the spine up to the base of the skull, includes the first 7 vertebrae. The intermediate 12 bones are thoracic vertebrae, and connect to the lower spine comprising the 5 lumbar vertebrae. The base of the spine is a sacral bones (including the coccyx).

The spinal column of bones is high complex in that it includes the over 20 bones coupled to one another, housing and protecting critical elements of the nervous system having innumerable peripheral nerves and circulatory bodies in close proximity. Despite its complexity, the spine is a highly flexible structure, capable of a high degree of curvature and twist in nearly every direction.

Genetic or developmental irregularities, trauma, chronic stress, tumors and disease, however, can result in spinal pathologies which either limit this range of motion, or which threatens the critical elements of the nervous system housed within the spinal column. A variety of systems have been disclosed in the art which achieve this immobilization by implanting artificial assemblies in or on the spinal column. These assemblies may be classified as anterior posterior or lateral implants. Lateral and anterior assemblies are coupled to the anterior portion of the spine which is in the sequence of vertebral bodies. Posterior implants generally comprise pairs of rods, which are aligned along the axis which the bones are to be disposed, and which are then attached to the spinal column by either hooks which couple to the lamina or attach to the transverse processes, or by screws which are inserted through the pedicles. In order to provide enhanced torsional rigidity, these implants generally include cross-connecting devices which couple the rods together transverse to the axis of the implants. These cross-connecting devices may couple directly to the rods themselves, or may be attached to the pedicle screws.

It is desirable to provide cross-connecting devices that are adjustable and can form angular installments using rotatable hooks. It is further desirable to provide a cross-connecting device with surgical screws for ease of installment.

SUMMARY OF THE INVENTION

The present invention relates to a surgical cross-connecting apparatus. The apparatus comprises a first element, a second element, an adjustable tightening device and at least two rotatable hook elements. The first element has opposing ends, one end has at least one aperture and the other end has a recessed surface which includes a central bore. The second element had two opposing ends, one end has at least one aperture and the other end has a recessed surface with an elongated aperture. The recessed surface of the second element is positioned to overlap the recessed surface of the first element. The tightening device is positioned through the elongated aperture of the second element and within the central bore of the first element to secure the second element onto the first element. The tightening device is designed to rotatably fit and slidably move within the elongated aperture of the second element. The rotatable hooking element comprises a hook and an adjustable securing device; each of the hooking devices being inserted within the apertures of the first and second elements. Since the hooking elements of the present invention are rotatable, the apparatus of the present invention, particularly the first and second elements, can form advantageous angular positions. The angular position allows the surgeons the ability to make a multitude of adjustments during installment of the apparatus. The angular positions may minimize or completely eliminate the need to remove boney sections of the vertebrae body during the installment process. In another embodiment, the securing device comprises a housing and a protruding element and during the securing process, the protruding element is swaged or flared outwardly to secure the securing device onto the hooking elements. In still another embodiment, the securing device of the rotatable hooking element is factory set.

In another embodiment, the central bore of the recessed surface of the first element includes a protruding member and the protruding member is designed to rotatably fit and slidably move within the elongated aperture of the second element.

In yet another embodiment, the tightening device comprises a threaded shaft and a head. In still another embodiment, the head of the tightening device comprises a recess coaxial to the shaft and designed to engage a fastening device. In still yet another embodiment, the recess is hexagon-shaped and the fastening device is a hexagon socket screw key.

In a further embodiment, the securing device of the hooking element comprises an aperture coaxial to the hook and designed to engage a fastening device. In still a further embodiment, the aperture of the securing device of the hooking element is hexagon-shaped and the fastening device is a hexagon socket screw key. In yet a further embodiment, the apparatus of the present invention further comprises a plurality of implantation rods whereby the rods are positioned within the hooks.

In another embodiment, the present invention relates to a cross-connecting surgical screw system. In still another embodiment, the system comprises a first element, a second element, an adjustable tightening device and at least two surgical screw devices. In yet another embodiment, the first element has opposing ends, one end having a first surgical screw system and the other end having a recessed surface with a central bore. The second element has opposing ends, one end has a surgical screw and the other end has a recessed surface with an elongated aperture. The recessed surface of the second element is positioned to overlap the recessed surface of the first element. The adjustable tightening device is positioned through the elongated aperture of the second element and within the central bore of the first element to secure the second element onto the first element. The tightening device is designed to rotatably fit and slidably move within the elongated aperture by the second element. Each of the first and second surgical screw devices comprises a screw at one end and a rod securing channel at the other end. In this embodiment, the screw is stationary and monoaxial.

In still another embodiment, the surgical screw device includes a locking device for securing the rod within the rod securing element. In yet another embodiment, each of the first and second surgical screw devices comprises a screw member, a receiver member, a pressure cap and a locking device. In one embodiment, the screw member, receiver member and pressure cap are factory set. In still yet another embodiment, the screw member comprises a head and a shaft; the head of the screw member has a spherical undersurface and a conical tapered recess. In a further embodiment, the receiver member has upper and lower portions, a u-shaped rod receiving channel, and an axial bore. In still a further embodiment, the u-shaped channel has two lateral legs at the upper portion of the receiver member and forms an opening leading to the axial bore. In yet a further embodiment, the axial bore near the lower portion of the receiver member includes an inwardly conical tapered surface, and the conical tapered surface has a diameter larger than the shaft of the screw member and a diameter smaller than the head of the screw member. The conical tapered surface forms a support upon which the spherical undersurface of the head of the screw member rests when the screw member is guided through the bore to the lower portion of the receiver member. In still yet a further embodiment, the pressure cap is positioned within the axial bore of the receiver member and is situated upon the head of the screw member. The pressure cap has upper and lower ends, the upper end of the cap comprises a concave radial portion upon which the rod is positioned and the lower end comprises a spherical portion situated upon the conical tapered recess of the head of the screw member. In another embodiment, the locking device is designed for securing the rod within the u-shaped channel of the receiver member and is locked by applying a tightening torque upon the rod when positioned within the opening and the bore near the upper portion of the receiver member. In this embodiment, the screw member is adjustable, multiaxial and rotatably about the support of the receiver member.

In still another embodiment, the central bore of the recessed surface of the first element includes a protruding member and the protruding member is designed to rotatably fit and slidably move within the elongated aperture of the second element. In yet another embodiment, the tightening device comprises a threaded shaft and a head. In still yet another embodiment, the head of the tightening device comprises a recess coaxial to the shaft and designed to engage a fastening device. In a further embodiment, the recess is hexagon-shaped and the fastening device is a hexagon socket screw key.

In still yet a further embodiment, the undersurface of the head and the shaft of the screw member comprises threaded portions. In still yet another embodiment, the conical tapered recess of the head of the screw member comprises an aperture coaxial to the shaft and designed to engage a fastening device. In another embodiment, the pressure cap further comprises an axial bore extending from the upper through the lower end of the cap; the bore of the cap corresponds to the aperture of the head of the screw member allowing an access for the fastening device.

In still another embodiment, the receiver member further comprises a rectangular key-locking segment and a cylindrical undercut situated adjacent to the bore; the pressure cap further comprises a cylindrical undercut and a retaining ring; the key-locking segment and the undercut of the receiver member is designed to engage the undercut and the ring of the cap to form an anti-rotation and locking mechanism. In yet another embodiment, the axial bore of the receiver member comprises a threaded portion and the locking device further comprises a corresponding threaded portion. In still yet another embodiment, the locking device is a set screw and in another embodiment, the locking device is a top locking nut.

In a further embodiment, the aperture of the head of the screw member is hexagon-shaped and the fastening device is a hexagon socket screw key.

In still a further embodiment, the legs of the u-shaped channel of the receiver member comprises a plurality of slots descending down the bore and the locking device comprises at least one protrusion designed to engage at least one of the slots of the legs of the u-shaped channel of the receiver member to secure the locking device within the receiver member.

In another embodiment, the locking device comprises a top and bottom portion wherein the bottom portion has a convex recess designed for contacting the curvature of the rod.

The present invention also relates to a surgical cross-connecting apparatus comprising a first element, a second element and at least two rotatable hooking elements. In one embodiment, the first element of the apparatus has opposing ends, one end having at least one aperture and the other end of the first element has a protrusion. In another embodiment, the second element has opposing ends, one end has at least one aperture and the other end of said second element having a protrusion receiving element. In still another embodiment, the protrusion of the first element is designed to fit within said protrusion receiving element of the second element. In yet another embodiment, the hooking elements comprise a hook and an adjustable device, and each of the hooking elements is situated within the aperture of the first and second elements.

In a further embodiment, the protrusion is bendable such that upon insertion of the protrusion into the protrusion receiving element, the first and second elements form an angle during installment of the apparatus onto a patient. In still a further embodiment, the protrusion is bent prior to insertion of the protrusion into the protrusion receiving element. In yet a further embodiment, the protrusion is bent after insertion of the protrusion into the protrusion receiving element. In still yet another embodiment, the first and second elements form an angle less than 180°.

In another embodiment, the apparatus further comprises a securing device and the protrusion receiving member of the second element includes an aperture for receiving the securing device. In still another embodiment, the securing device is a set screw.

In yet another embodiment, the protrusion receiving element comprises a central bore for receiving the protrusion. In still yet another embodiment, the protrusion comprises an aperture corresponding to the aperture of the protrusion receiving member for receiving the securing device.

In a further embodiment, the protrusion of the first element has a flat top surface for contacting the securing device. In still a further embodiment, the protrusion receiving element is designed to be bent during the installation process.

The present invention also relates to a method of securing at least two implantation rods. In one embodiment, the method comprises: providing a cross-connecting apparatus having first and second elements, an adjustable tightening device and at least two rotatable hooking elements; attaching the hooking device onto the rods and securing the hooking system using an adjustable securing device; adjusting the distance between the first and second hooking devices by sliding a tightening device along an elongated aperture of the second element to a predetermined position; and securing the first and second elements to the predetermined position using the tightening device. In one embodiment, the predetermined position is achieved when the first and second elements form an angle. In another embodiment, the angle is less than 180°.

In still another embodiment, the first element has opposing ends, one end having at least one aperture and the other end has a recessed surface with a central bore. In yet another embodiment, the second element has opposing ends, one end having at least one aperture and the other end having a recessed surface with an elongated aperture; the recessed surface of the second element being positioned to overlap the recessed surface of the first element. In still yet another embodiment, the adjustable tightening device is positioned through the elongated aperture of the second element and within the central bore of the first element to secure the second element onto the first element; the tightening device being designed to rotatably fit and slidably move within the elongated aperture of the second element. In a further embodiment, the two rotatable hooking elements comprise a hook and an adjustable securing device; each of the hooking devices being inserted with the aperture of the first and second elements.

In still a further embodiment, the central bore of the recessed surface of the first element includes a protruding member and the method includes designing the protruding member to rotatably fit and slidably move within the elongated aperture of the second element.

The present invention also relates to a method of attaching a surgical screw onto a bone and securing at least two implantation rods. In one embodiment, the method comprises providing a cross-connecting surgical screw system comprising a first element with opposing ends, one end having a first surgical screw device and the other end having a recessed surface with a central bore; a second element with opposing ends, one end having a second surgical screw device and the other end having a recessed surface with an elongated aperture, the recessed surface of the second element being position to overlap the recessed surface of the first element; an adjustable tightening device positioned through the elongated aperture of the second element and with the central bore of the first element to secure the second element onto the first element, the tightening device being designed to rotatably fit and slidably move within the elongated aperture of the second element; each of the first and second surgical screw devices comprising a screw member, a rod receiving element, and a locking device; attaching each of the screw members of the surgical screw device into a bone; inserting a rod within the rod receiving element of the surgical screw device; securing the rod within the rod receiving element using the locking device; adjusting the distance between the first and second surgical screw device by sliding the tightening device along the elongated aperture of the second element to a predetermined position; and securing the first and second elements to the predetermined position using the tightening device. In another embodiment, the predetermined position includes the first and second elements forming an angle. In still another embodiment, the angle is less than 180°.

In yet another embodiment, the surgical screw devices comprises a screw member having a head and a shaft, the head of the screw member having a spherical undersurface and a conical tapered recess; a receiver member having upper and lower portions, a u-shaped rod receiving channel, and an axial bore; the u-shaped channel has two lateral legs at the upper portions of the receiver member and forms an opening leading to the axial bore; the axial bore means the lower portion of the receiver member including an inwardly conical tapered surface, the conical surface having a diameter longer than the shaft of the screw member and a diameter smaller than the head of the screw member; the conical surface forming a support upon which the spherical undersurface of the head of the screw member rests when the screw member is guided through the bore of the lower portion of the receiver member; a pressure cap positioned within the axial bore of the receiver member and situated upon the head of the screw member; the pressure cap having upper and lower ends, the upper end of the cap comprising a concave radial portion upon which the rod is positioned, the lower end comprising a spherical portion situated upon the conical tapered recess of the head of the screw member; and the locking device for securing the rod within the u-shaped channel of the receiving member by applying a tightening torque upon the rod when positioned within the opening and the bore near the upper portion of the receiver member.

The convex spherical/concave conical taper interface of the present invention occurs at two instances: (a) the spherical undersurface of the head of the screw member and the conical tapered recess surface of the receiver member and (b) the spherical portion of the pressure cap and the conical tapered recess of the head of the screw member. The convex spherical/concave conical taper interface at each junction of the locking mechanism of the present invention are wedge jointly. This wedge joint is achieved when a changing force is applied and the convex spherical features is compressed into the concave conical taper feature. At the periphery point contacts and at the component interfaces, a resultant hoop stress is created. This hoop stress has a wedging effect at the component interfaces, thereby consistently locking the device in position. In addition to the wedging effect, the present invention also provides a mechanical leverage. The wedging effect and mechanical leverage provides for a constantly robust locking mechanism. The consistency is based upon the reproducible nature of the tapered nest geometry. Even when considering tolerance, the taper lock wedging effect and leverage position will always be consistently achieved. If any tolerance variation is encountered, this will translate into a slight variation of height in the longitudinal axis of the assembly which is negligible as to the function of the locking mechanism and the final device assembly.

BRIEF DESCRIPTION OF THE DRAWINGS

A more complete appreciation of the present invention and many of the attendant advantages thereof will be readily understood by reference to the following description when considered in connection with the accompanying drawings in which.

Among those benefits and improvements that have been disclosed, other objects and advantages of this invention will become apparent from the following description taken in conjunction with the accompanying drawings. The drawings constitute a part of this specification and include exemplary embodiments of the present invention and illustrate various objects and features thereof.

DETAILED DESCRIPTION OF THE DRAWINGS

Figure 1:
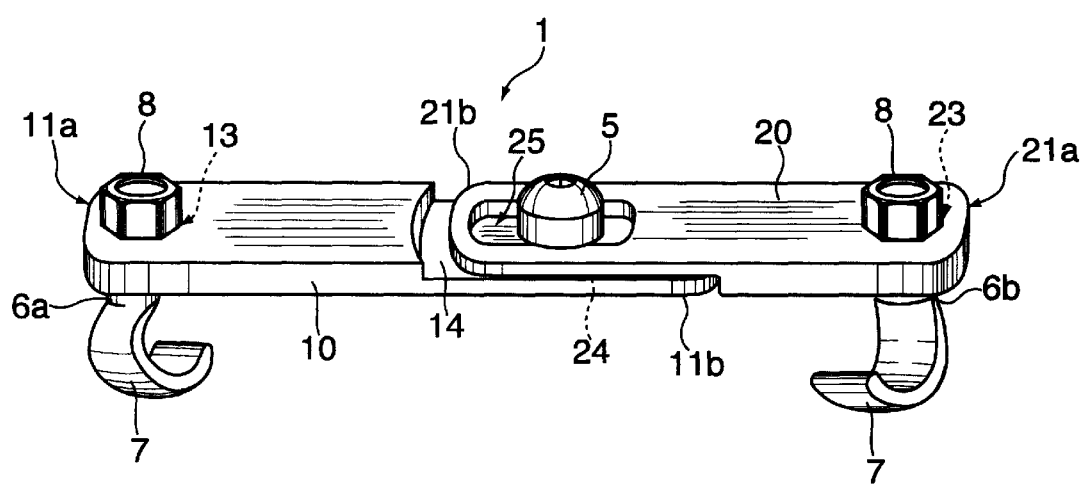
FIG. 1 is a perspective view of the surgical cross-connecting apparatus of the present invention.
Figure 2:
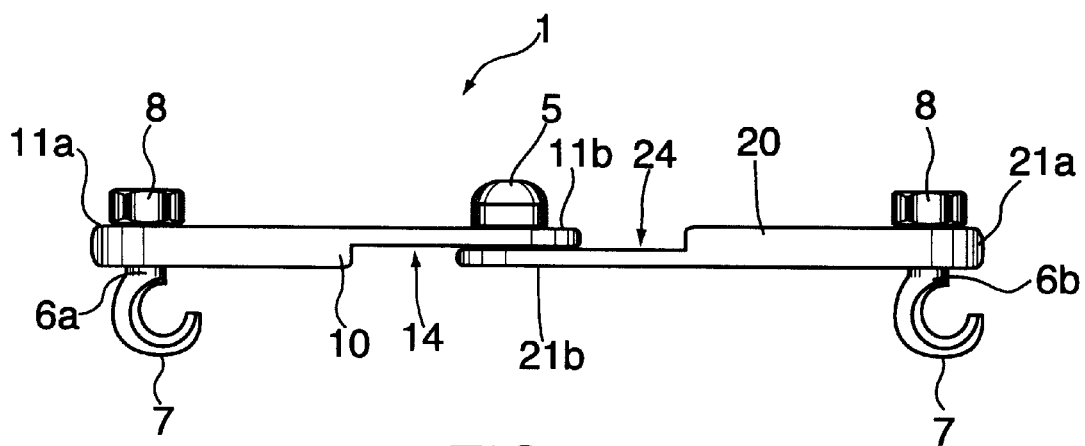
FIG. 2 is a side view of the surgical cross-connecting apparatus.

Referring now to the drawings wherein like reference numerals designate identical or corresponding parts throughout the several views, and more particularly to FIG. 1 and FIG. 2 wherein the surgical cross-connecting apparatus 1 of the present invention is illustrated. The apparatus 1 comprises a first element 10, a second element 20, an adjustable tightening device 5 and at least two hooking elements, 6a and 6b, respectively. The first element 10 has opposing ends, 11a and 11b, one end 11a has at least one aperture 13 and the other end 11b has a recess surface 14 with a central bore. The second element 20 has opposing ends, 21a and 21b, one end 21a having at least one aperture 23 and the other end 21b has a recessed surface 24 which includes an elongated aperture 25. The recessed surface 24 of the second element 20 is positioned to overlap the recessed surface 14 of the first element 10. The adjustable tightening device 5 is positioned through the elongated aperture 25 of the second element 20 and within the central bore of the first element 10 to secure the second element 20 onto the first element 10. The tightening device 5 is designed to rotatably fit and slidably move within the elongated aperture 25 of the second element 20. Each of the two rotatable hooking elements, 6a and 6b, comprises a hook 7 and an adjustable securing device 8. Each of the hooking devices, 6a and 6b, are inserted within the apertures, 13 and 23, of the first and second elements, 10 and 20, respectively.

Figure 3:
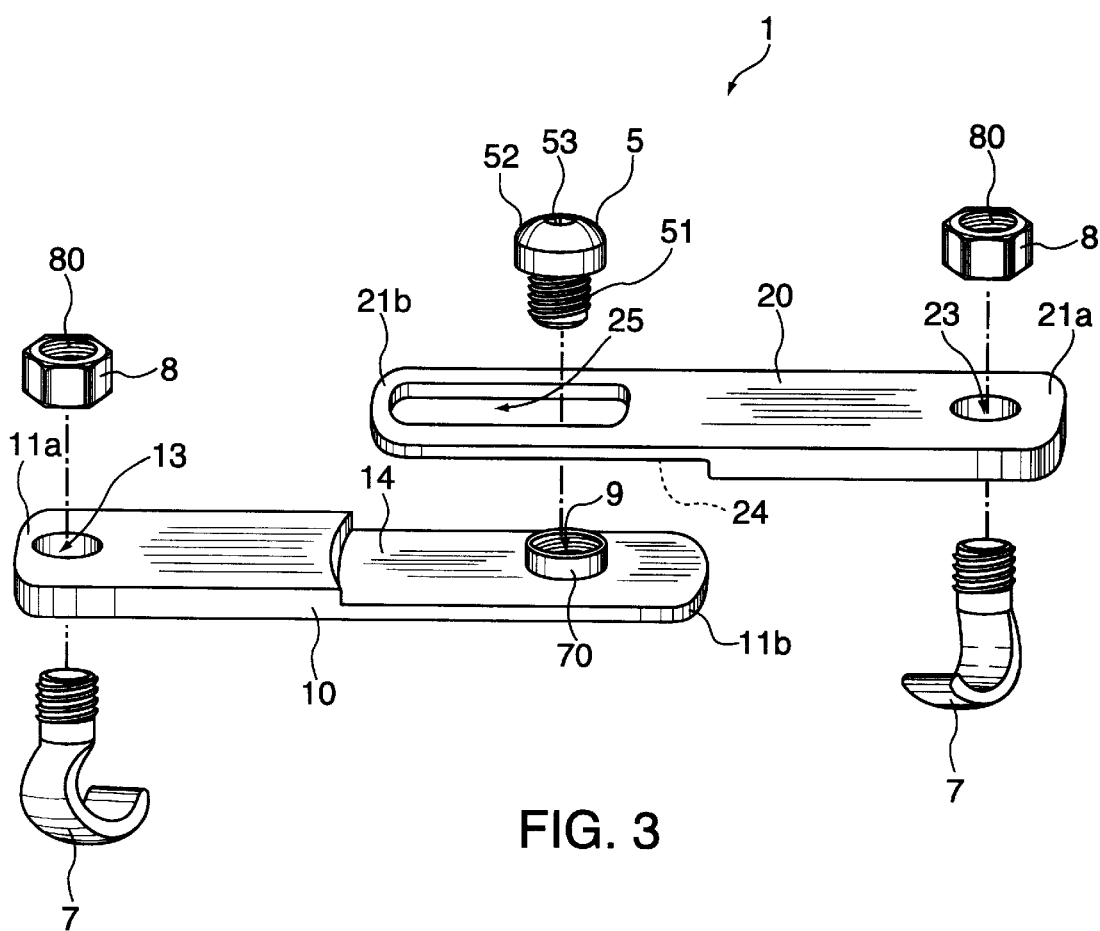
FIG. 3 is a perspective view of the unassembled surgical cross-connecting apparatus of the present invention.

FIG. 3 depicts a perspective view of the surgical cross-connecting apparatus 1 of the present invention in an unassembled form. The apparatus 1 comprises the first element 10 having opposing ends, 11a and 11b, one end 11a has at least one aperture 13 and the other end 11b has a recessed surface 14 which has a central bore 9. The apparatus 1 also comprises the second element 20 having opposing ends, 21a and 21b, one end 21a has at least one aperture 23 and the other end has a recessed surface 24. The recessed surface 24 includes an elongated aperture 25. The recessed surface 24 of the second element 20 is positioned to overlap the recessed surface 14 of the first element 10. The apparatus further comprises an adjustable tightening device 5 which is positioned through the elongated aperture 25 of the second element 20 and within the central bore 9 of the first element 10 to secure the second element 20 onto the first element 10. The tightening device 5 is designed to rotatably fit and slidably move with the elongated aperture 25 of the second element 20. The apparatus 1 further comprises at least two rotatable hooking elements, 6a and 6b, respectively, and each element comprises a hook 7 and an adjustable securing device 8. The hooking elements, 6a and 6b, are inserted within the aperture 13 and 23, of the first and second elements, 10 and 20.

The central bore 9 of the recessed surface 14 of the first element 10 includes a protruding member 70 and in one embodiment, the protruding member 70 is designed to rotatably fit and slidably move within the elongated aperture 25 of the second element 20.

The tightening device 5 of the apparatus 1 comprises a threaded shaft 51 and a head 52. The head 52 of the tightening device 5 comprises a recess 53 coaxial to the shaft 51 and designed to engage a fastening device. In another embodiment, the recess 53 is hexagon-shaped and the fastening device is a hexagon socket screw key.

In still another embodiment, the securing device 8 of each of the hooking element, 6a or 6b, comprises an aperture 80 coaxial to the hook 7 and designed to engage a fastening device. In yet another embodiment, the aperture 80 of the securing device 8 of each of the hooking elements, 6a or 6b, is hexagon-shaped and the fastening device is a hexagon socket screw key. The hooks 7 may be rotationally adjustable at 360°. The securing device 8 may be a locking nut.

FIGS. 4a–4e depict various angular views of the surgical cross-connecting apparatus 1 of the present invention in use with implantation rods 30. The hooks 7 of the hooking elements, 6a or 6b, are attached onto the rods 30 and the hooks 7 are secured to the rods 30 using the adjustable securing device 8.

The distance between the first and second hooking elements, 6a and 6b respectively, are adjusted by sliding the tightening device 5 along the elongated aperture 25 of the second element 20 to a predetermined position and finally, the first and second elements, 10 and 20, are secured at the predetermined position using the tightening device 5.

Figure 4A:
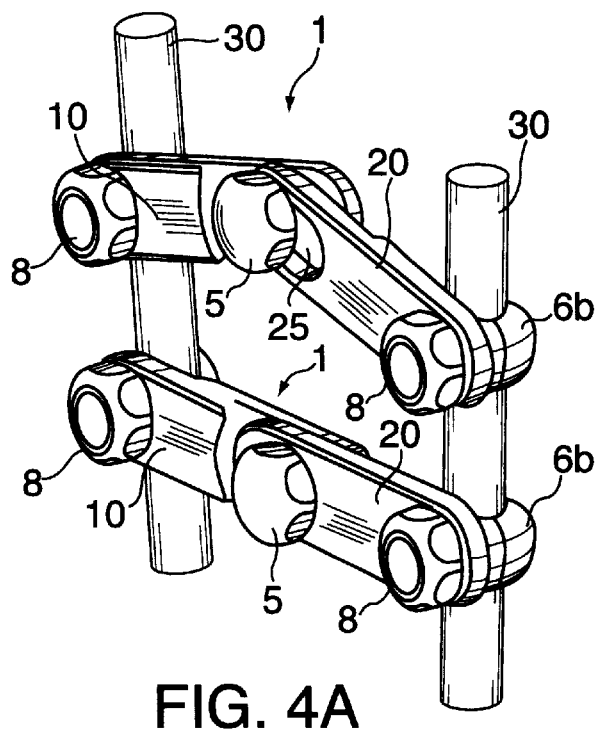
FIGS. 4a–4e depict various angular views of the surgical cross-connecting apparatus in use with implantation rods and in angular positions.
Figure 4B:
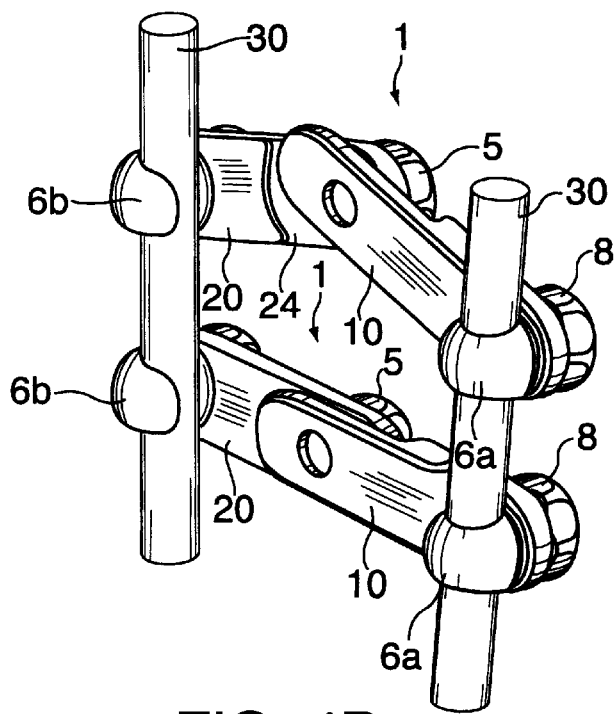
Figure 4C:
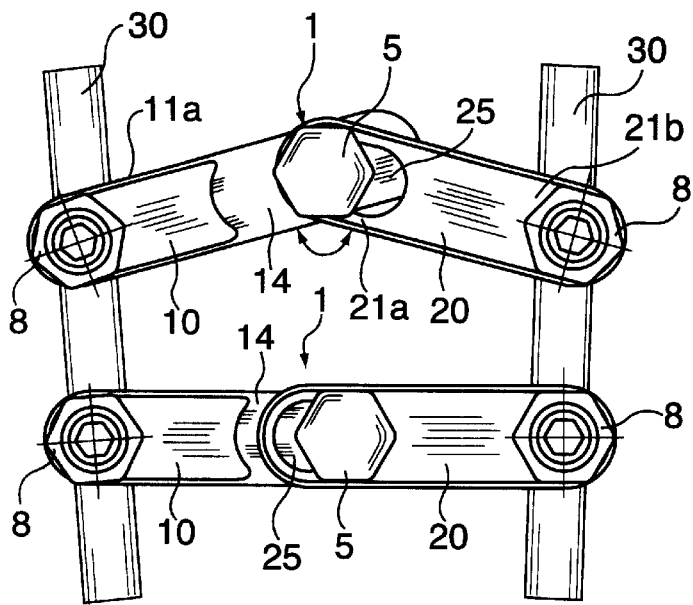
Figure 4D:
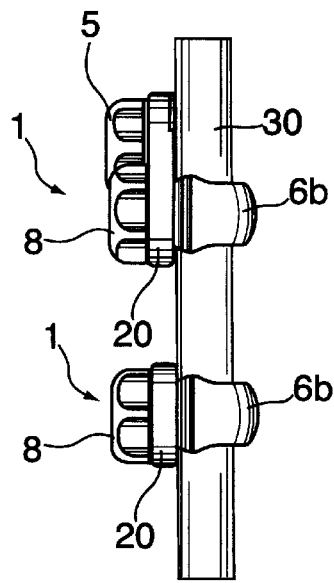
Figure 4E:
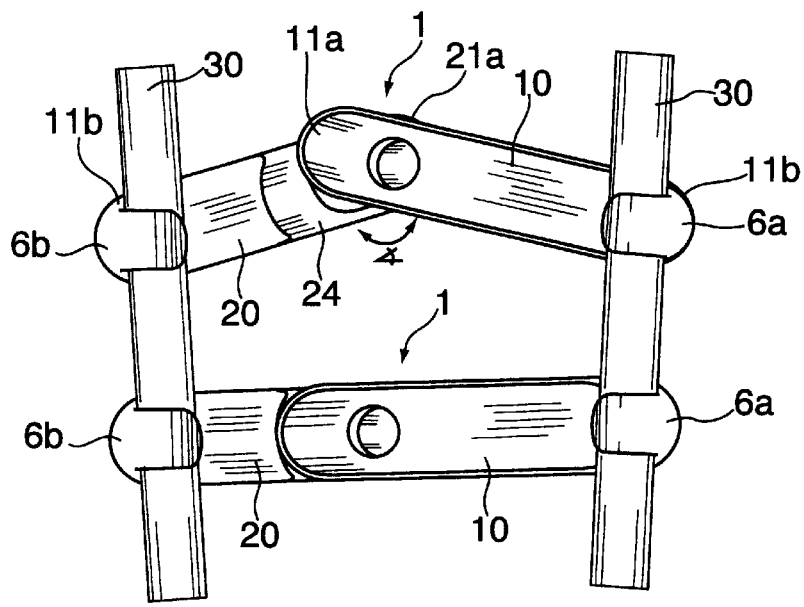
Figure 5B:
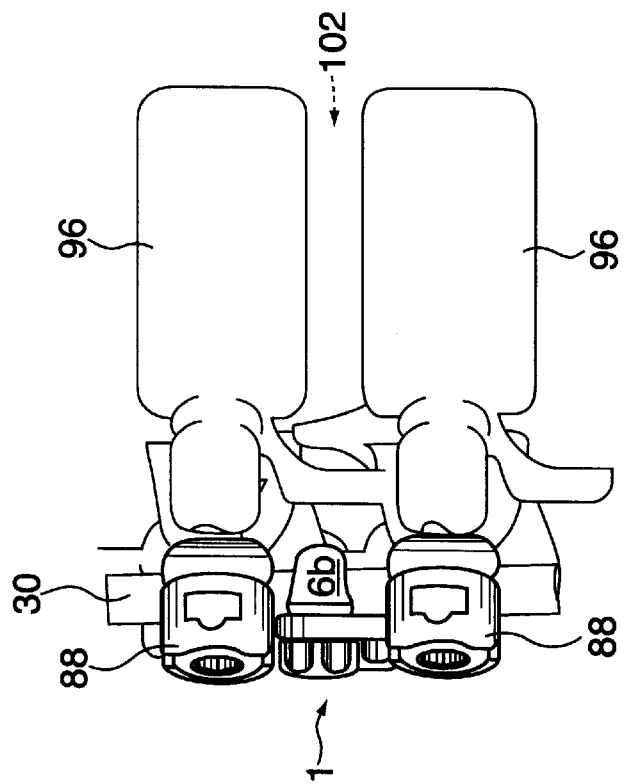
FIGS. 5a–5d depict various angular views of the surgical cross-connecting apparatus assembled with implantation rods and surgical screws in the human vertebrae.
Figure 5A:
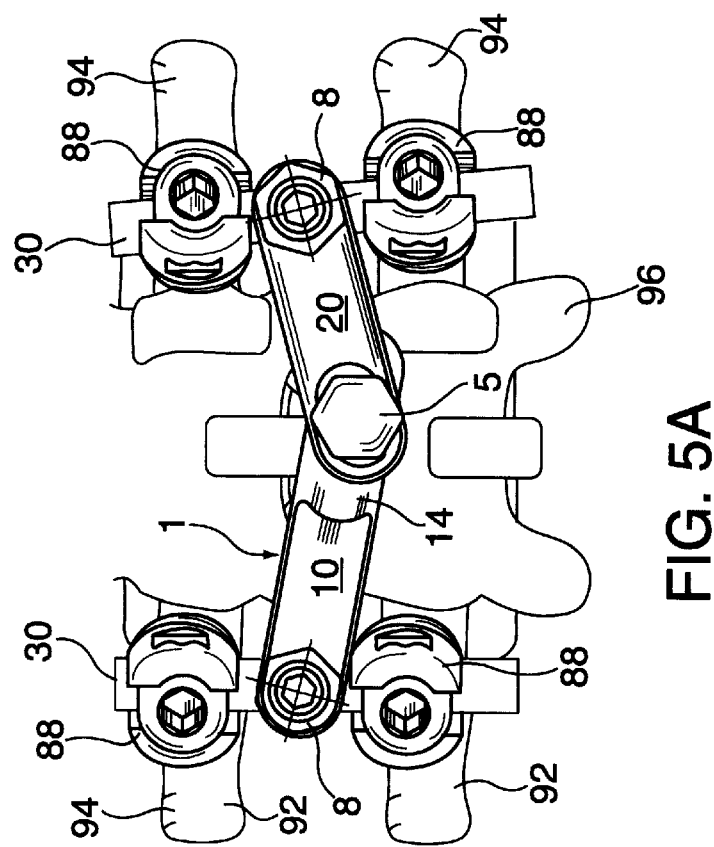
Figure 5D:
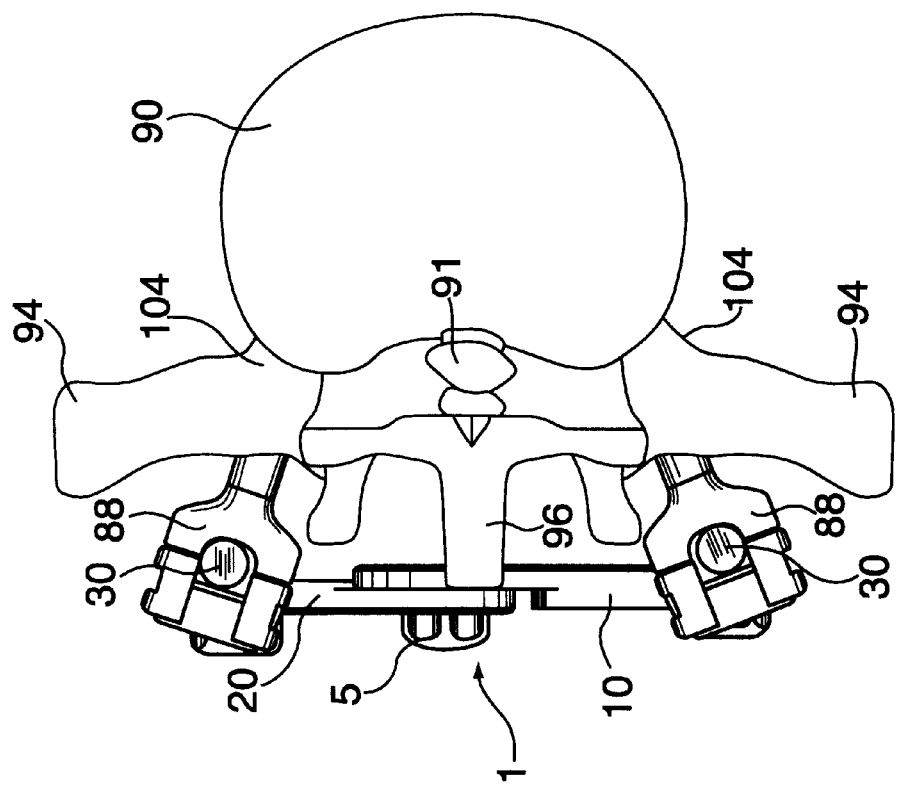
Figure 5C:
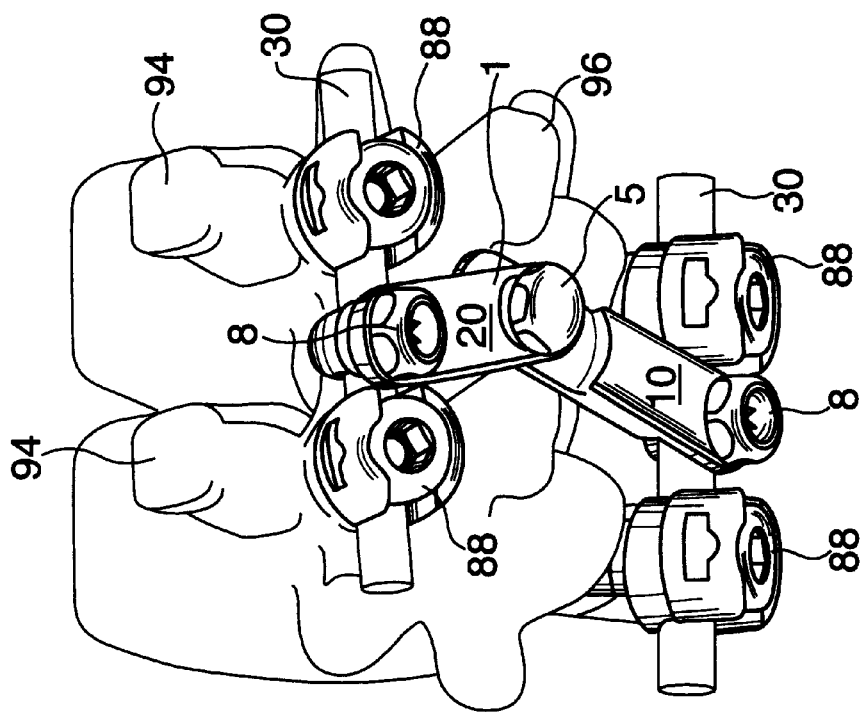

FIGS. 4c and 4e also illustrate the advantage of the apparatus 1 of the present invention to form angular position during installation with implantation rods. The first and second elements, 10 and 20, rotate about the tightening device 5 and form angles ∢. In one embodiment, the angle ∢ is less than 180°. In the angled position, the end 21b of the second element 20 will no longer be perpendicular to the end 11b of the first element 10. The apparatus 1 of the present invention provides for a linear adjustment as well as a degree of rotational adjustment allowing the surgeon greater inter-operative flexibility. The rotational adjustments or angular positional capabilities of the present invention creates a robust construct. The angle also strengthens the implanted pedicle screw construct and prevents the buckling of the implantation rods 30. The linear and rotational adjustments of the apparatus 1 is dictated by the position of the rods 30.

The apparatus 1 also minimizes or completely eliminates the osteotomy of the spinous process during surgery. An osteotomy is performed during surgery to remove a larger section of boney prominence of the posterior aspect of each vertebrae body. At minimum, the apparatus 1 of the present invention allows for a more conservative osteotomy of the spinous process and great inter-operative flexibility. Under certain circumstances, the apparatus avoids the osteotomy of spinous process because of the multiple of inter-operative angular adjustments available to the surgeon.

FIG. 5 depicts various angular views of the cross-connecting apparatus 1 of the present invention in use with implantation rods 30 and surgical screws 8 and installed onto the human vertebrae body. The spinal cord is housed in the central canal 91, and protected from the posterior side by a shell of bone called the lamina 92. The lamina 92 includes a rearwardly and downwardly extending portion called the spinous process 96 and laterally extending structures called the transverse processes 94. The anterior portion of the spine comprises a set of generally cylindrically shaped bones which are stacked one on top of the other. These portions of the vertebrae are referred to as the vertebral bodies 90, and are each separated from the other by intervertebral discs 102. The pedicles 104 comprises bone bridges which couple the anterior vertebral body 90 to the corresponding lamina 92.

The surgical screw 88 is affixed into the pedicles 104 and the implantation rods 30 are positioned onto the rod receiving element of the screws 88. The cross-connecting apparatus 1 of the present invention is then secured onto the rods 30. The apparatus 1 comprises a first and second element, 10 and 20 respectively, and are connected by an adjustable tightening device 5. The elements 10 and 20 have hooking elements, 6a and 6b, with securing devices 8. The hooking elements attach onto the rods 30. In one embodiment, the elements 10 and 20 can form angular predetermined positions.

Figure 6:
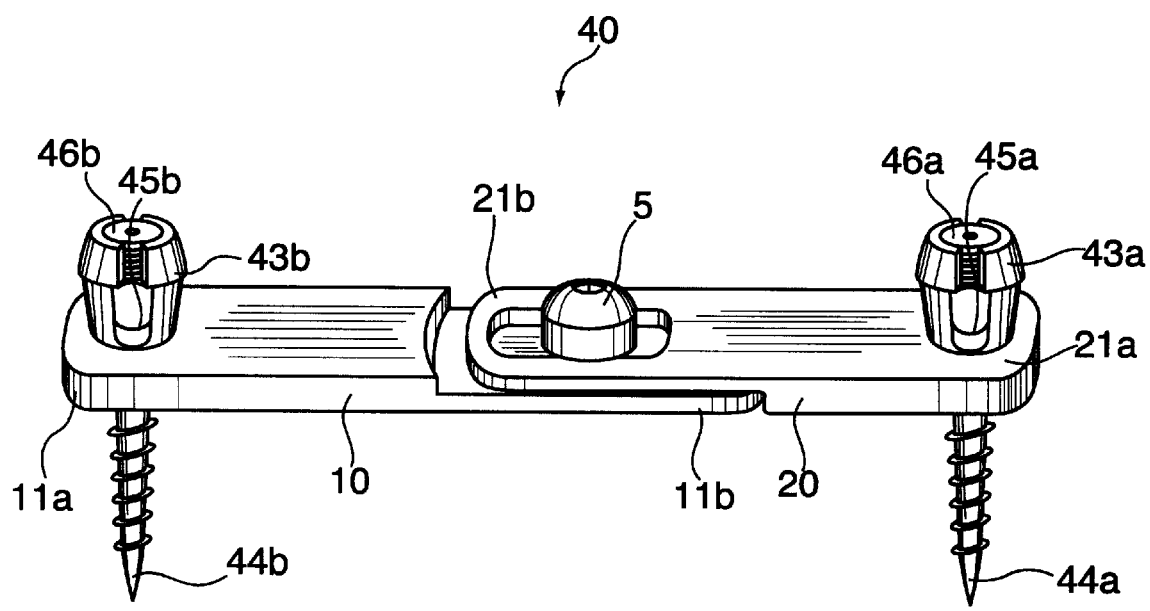
FIG. 6 is a perspective view of the cross-connecting surgical screw system.
Figure 7:
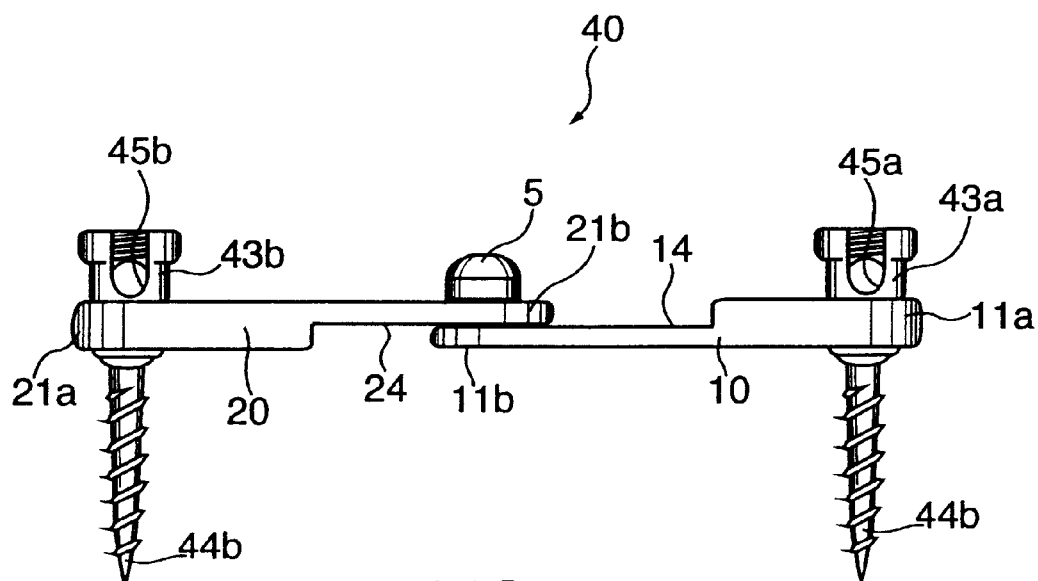
FIG. 7 is a side view if the cross-connecting surgical screw system.
Figure 8:
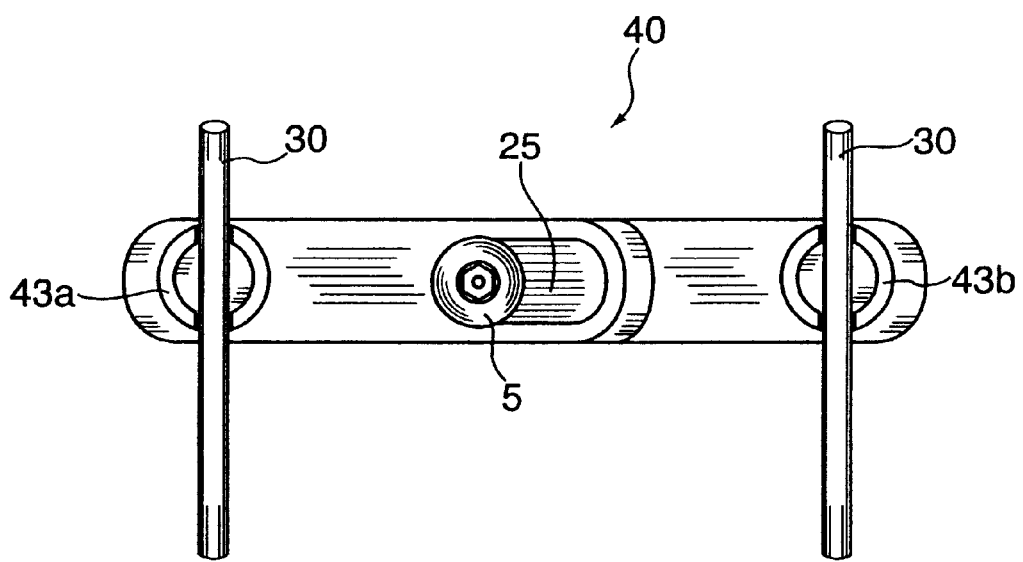
FIG. 8 is an overhead view of the cross-connecting surgical screw system in use with implantation rods.

FIG. 6, FIG. 7 and FIG. 8 depict the cross-connecting surgical screw system 40 of the present invention. The system 40 comprises a first element 10 having opposing ends, 11a and 11b; one end 11a has a first surgical screw device 43b and the other end has a recessed surface 14 with a central bore. The system 40 also comprises a second element 20 having opposing ends, 21a and 21b; one end 21a having a second surgical screw system 43a and the other end 21b having a recessed surface 24 with an elongated aperture 25. The recessed surface 24 of the second element 20 is positioned to overlap the recessed surface 14 of the first element 10. The tightening device 5 is positioned through the elongated aperture 25 of the second element 20 and within the central bore 9 of the first element 10 to secure the second element 20 onto the first element 10. The tightening device 5 is designed to rotatably fit and slidably move within the elongated aperture 25 of the second element 20. Each of the first and second surgical screw device, 43a and 43b, comprises a screw member, 44a or 44b, and rod receiving element, 45a or 45b. The device, 43a or 43b, also comprise a locking device, 46a or 46b, for securing a rod 30 within the rod securing element 45a or 45b.

Figure 9A:
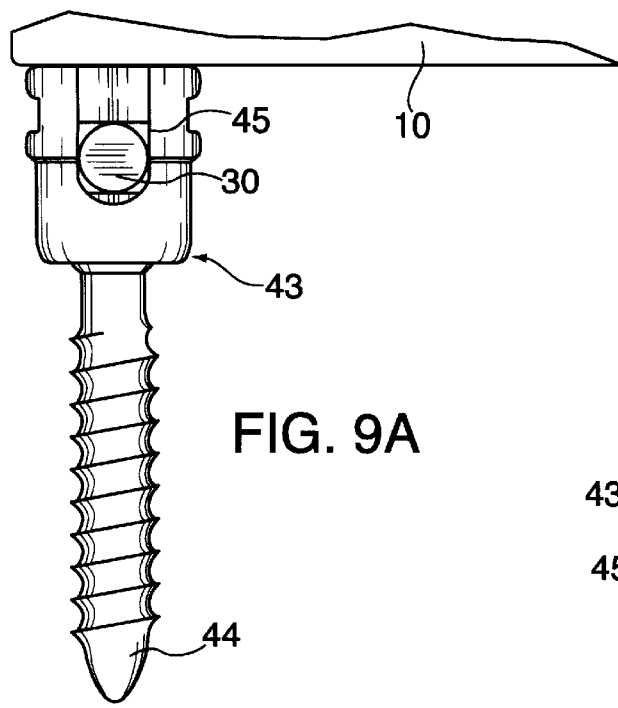
FIGS. 9a–c depicts various perspective views of difference embodiments of the surgical screw devices of the cross-connecting surgical screw system of the present invention.
Figure 9B:
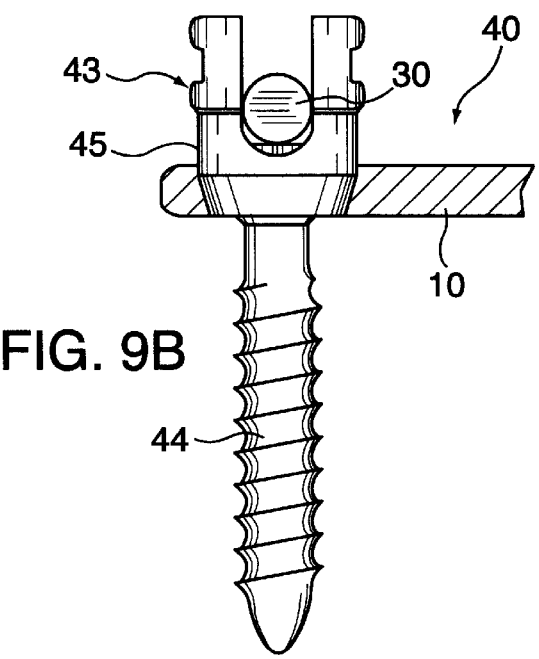
Figure 9C:
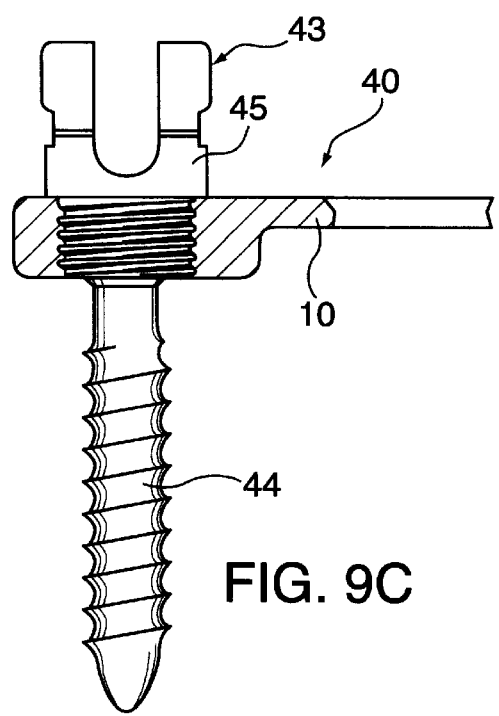

FIGS. 9a–c illustrate different embodiments of the surgical screw device 43 of the present invention. The device 43 comprises a screw member 44, a rod receiving element 45 and a locking device 46. FIG. 9a depicts an embodiment wherein the rod receiving element 45 is below the first element 10 of the system 40; and the locking device 46 is a top loading screw clamp. FIGS. 9b–9c depicts an embodiment wherein the rod receiving element 45 is above the first element 10 of the system 40. FIG. 9b shows the device 43 is taper locked onto element 10. FIG. 9c shows the device 43 screw locked onto element 10.

Figure 10:
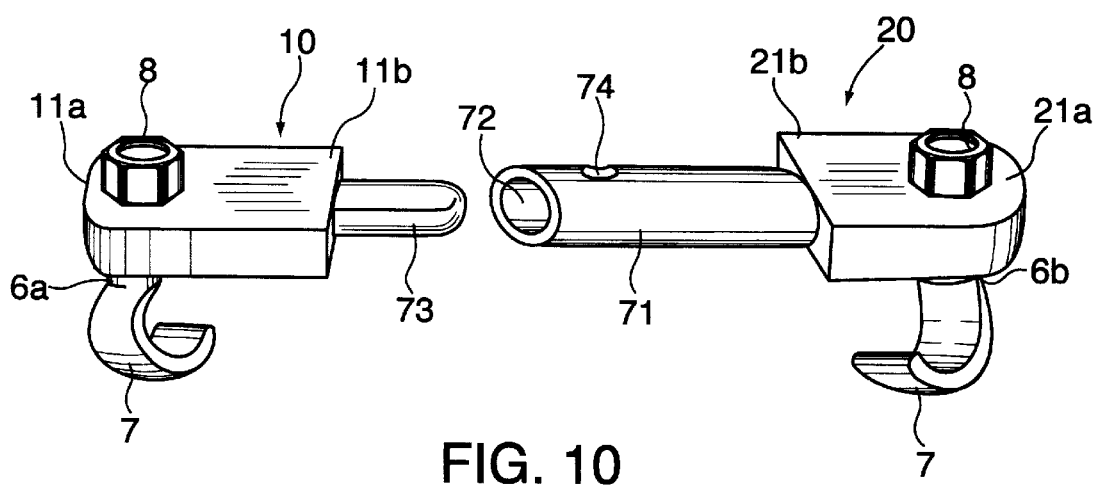
FIG. 10 is a perspective view of another embodiment of the cross-connecting apparatus of the present invention.

FIG. 10 is a perspective view of another embodiment of the present invention wherein the apparatus comprises a first and second element, 10 and 20, respectively, and at least two hooking elements, 6a and 6b. The first element 10 has opposing ends 11a and 11b; one end 11a has at least one aperture and the other end 11b has a protrusion 73. The second element 20 has opposing ends 21a and 21b, one end 21a has at least one aperture and the other end 21b has a protrusion receiving member 71. The receiving member has a central bore 72 designed for receiving the protrusion 73. The receiving member 71 also comprises an aperture 74 for receiving a securing device for securing the protrusion 73 within the protrusion receiving member 71. The protrusion 73 may be bent prior to or after insertion into the protrusion receiving member 71.

Figure 11:
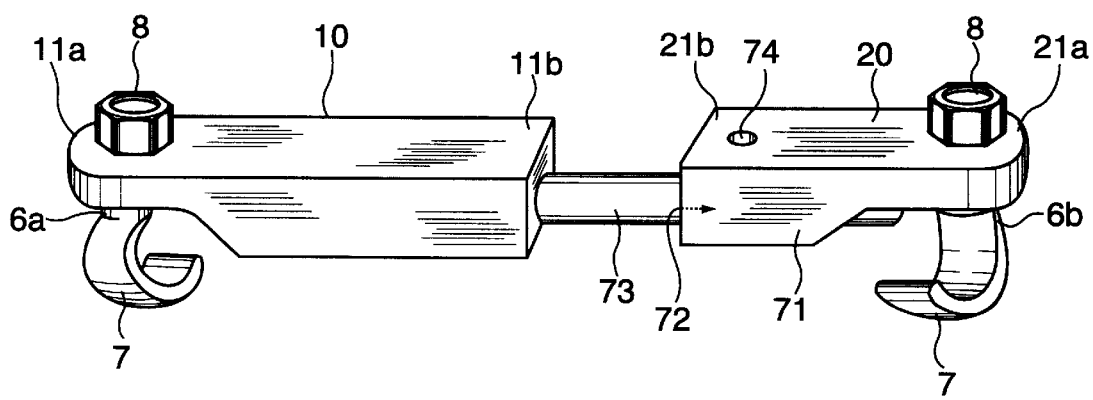
FIG. 11 is a perspective view of still another embodiment of the cross-connecting apparatus of the present invention.

FIG. 11 is a perspective view of still another embodiment of the present invention. The cross-connecting apparatus comprises first and second elements, 10 and 20, respectively, and at least two hooking elements, 6a and 6b. The first element 10 has opposing ends 11a and 11b; one end has at least one aperture and the other end 11b has a protrusion 73. The second element 20 has opposing ends, 21a and 21b; one end 21a has at least one aperture and the other end 21b has a protrusion receiving member 71. In one embodiment, the protrusion receiving member 71 is a housing having a central bore 72 for receiving the protrusion 73. The protrusion receiving member 71 comprises an aperture 74 and a securing device situated within the aperture to secure the first and second elements, 10 and 20.

Figure 12A:
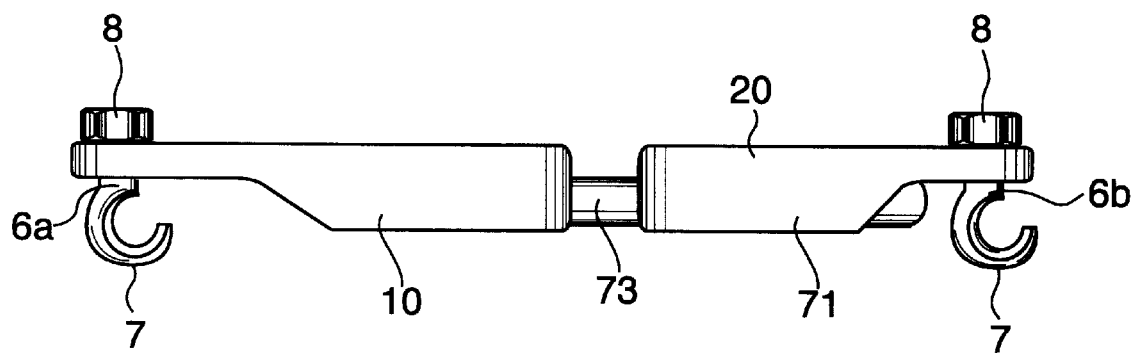
FIGS. 12a–c are side views of the embodiment of the cross-connecting apparatus depicted in FIG. 11 and the angular positions formed by the cross-connecting apparatus.
Figure 12B:
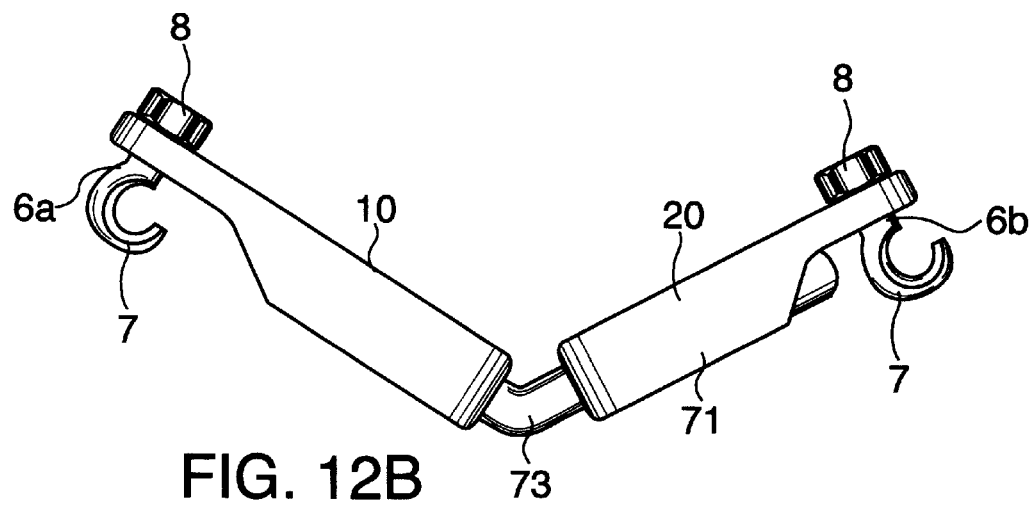
Figure 12C:
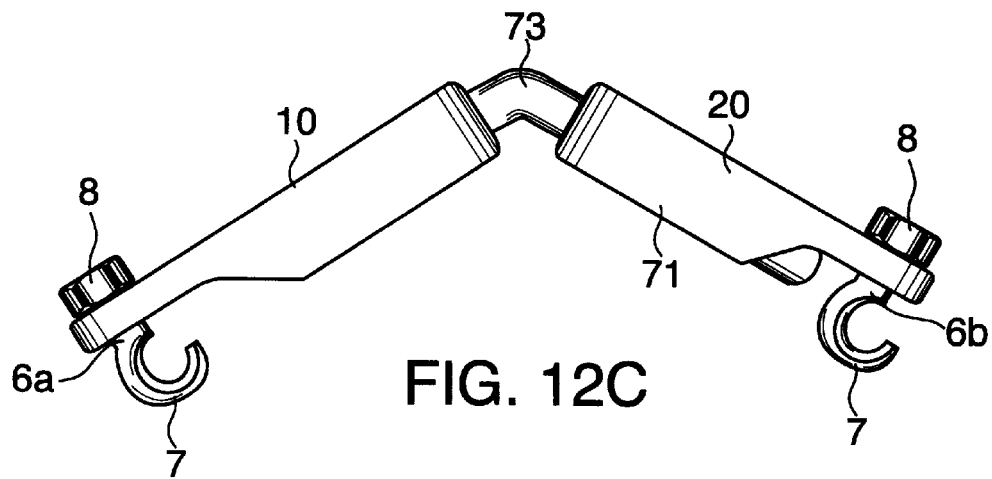

FIGS. 12a–c are side views of the cross-connecting apparatus of the present invention. The apparatus comprises a first element 10 having a hooking element 6a at one end and a protrusion 73 on the other end. The apparatus also comprises a second element 20 having a hooking element 6b at one end and a protrusion receiving element 71 on the other end. The protrusion 73 is situated within the protrusion receiving element 71 and secured with a securing device. FIG. 12b illustrates the protrusion 73 of the apparatus bent in an upward direction to create an angular position during installation of the apparatus. FIG. 12c depicts the protrusion 73 of the apparatus bent in a downward direction.

Numerous modifications and variations of the present invention are possible in light of the above teachings. It is therefore to be understood that within the scope of the attendant claims appended thereto, this invention may be practiced otherwise than as specifically disclosed herein.

What is claimed is:

1. A surgical cross-connecting apparatus, comprising:
   a first element having opposing ends, one end having at least one aperture, said other end of said first element having a recessed surface, said recessed surface including a central bore;
   a second element having opposing ends, one end having at least one aperture, said other end of said second element having a recessed surface, said recessed surface including an elongated aperture, said recessed surface of said second element being positioned to overlap said recessed surface of said first element;
   an adjustable tightening device positioned through said elongated aperture of said second element and within said central bore of said first element to secure said second element onto said first element, said tightening device being designed to rotatably fit and slidably move within said elongated aperture of said second element; and
   at least two rotatable hooking elements each comprising a hook and an adjustable securing device, each of said hooking elements being inserted within said apertures of said first and second elements.

2. The surgical cross-connecting apparatus of claim 1 wherein said central bore of said recessed surface of said first element includes a protruding member and said protruding member being designed to rotatably fit and slidably move within said elongated aperture of said second element.

3. The surgical cross-connecting apparatus of claim 1 wherein said tightening device comprises a threaded shaft and a head.

4. The surgical cross-connecting apparatus of claim 3 wherein said head of said tightening device comprises a recess coaxial to said shaft and designed to engage a fastening device.

5. The surgical cross-connecting apparatus of claim 4 wherein said recess is hexagon-shaped and said fastening device is a hexagon socket screw key.

6. The surgical cross-connecting apparatus of claim 1 wherein said securing device of said hooking elements comprising an aperture coaxial to said hook and designed to engage a fastening device.

7. The surgical cross-connecting apparatus of claim 6 wherein said aperture of said securing device of said hooking elements is hexagon-shaped and said fastening device is a hexagon socket screw key.

8. The surgical cross-connecting apparatus of claim 1 further comprising a plurality of implantation rods, said rods being positioned within said hooks.

9. A cross-connecting surgical screw system, comprising:
a first element having opposing ends, one end having a first surgical screw device, said other end of said first element having a recessed surface, said recessed surface including a central bore;
a second element having opposing ends, one end having a second surgical screw device, said other end of said second element having a recessed surface, said recessed surface including an elongated aperture, said recessed surface of said second element being positioned to overlap said recessed surface of said first element;
an adjustable tightening device positioned through said elongated aperture of said second element and within said central bore of said first element to secure said second element onto said first element, said tightening device being designed to rotatably fit and slidably move within said elongated aperture of said second element; and
each of said first and second surgical screw devices comprises a screw member and a rod receiving element.

10. The cross-connecting surgical screw system of claim 9 wherein said screw devices further include a locking device for securing a rod within the rod receiving element.

11. The cross-connecting surgical screw system of claim 9 wherein each of said first and second surgical screw devices comprising a screw member having a head and a shaft, said head of said screw member having a spherical undersurface and a conical tapered recess; a receiver member having upper and lower portions, a unshaped rod receiving channel, and an axial bore, said unshaped channel having two lateral legs at said upper portion of said receiver member and forming an opening leading to said axial bore; said axial bore near said lower portion of said receiver member including an inwardly conical tapered surface, said conical surface having a diameter larger than said shaft of said screw member and a diameter smaller than said head of said screw member, said conical surface forming a support upon which said spherical undersurface of said head of said screw member rests when said screw member is guided through said bore to said lower portion of said receiver member; a pressure cap positioned within said axial bore of said receiver member and situated upon said head of said screw member, said pressure cap having upper and lower ends, said upper end of said cap comprising a concave radial portion upon which the rod is positioned, said lower end comprising a spherical portion situated upon said conical tapered recess of said head of said screw member; and a locking device for securing the rod within said unshaped channel of said receiving member by applying a tightening torque upon the rod when positioned within said opening and said bore near said upper portion of said receiver member.

12. The system of claim 11 wherein said conical tapered recess of said head of said screw member comprising an aperture coaxial to said shaft and designed to engage a fastening device; said pressure cap further comprising an axial bore extending from said upper through said lower ends of said cap; said bore of said cap corresponding to said aperture of said head of said screw member allowing an access for said fastening device.

13. The system of claim 12 wherein said aperture of said head of said screw member is hexagon shaped and said fastening device is a hexagon socket screw key.

14. The system of claim 11 wherein said receiver member further comprising a rectangular key-locking segment and a cylindrical undercut situated adjacent to said bore; said pressure cap further comprising a cylindrical undercut and a retaining ring; said key-locking segment and said undercut of said receiver member being designed to engage said undercut and said ring of said cap to form an anti-rotation and locking mechanism.

15. The system of claim 11 wherein said axial bore of said receiver member further comprises a threaded portion and said locking device further comprises a corresponding threaded portion.

16. The system of claim 15 wherein said locking device is a set screw.

17. The system of claim 15 wherein said locking device is a top locking nut.

18. The system of claim 11 wherein said legs of said u-shaped channel of said receiver member comprises a plurality of slots descending down said bore and said locking device comprising at least one protrusion designed to engage at least one of said slots of said legs of said u-shaped channel of said receiving member to secure said locking device within said receiving member.

19. The system of claim 11 wherein said locking device comprises a top and bottom portion, said bottom portion having a convex recess designed for contacting the curvature of the rod.

20. The surgical system of claim 9 wherein said central bore of said recessed surface of said first element includes a protruding member and said protruding member being designed to rotatably fit and slidably move within said elongated aperture of said second element.

21. The cross-connecting apparatus of claim 9 wherein said tightening device comprises a threaded shaft and a head.

22. The cross-connecting apparatus of claim 21 wherein said head of said tightening device comprises a recess coaxial to said shaft and designed to engage a fastening device.

23. The cross-connecting apparatus of claim 22 wherein said recess is hexagon-shaped and said fastening device is a hexagon socket screw key.

24. The cross-connecting apparatus of claim 9 wherein each of said first and second surgical screw devices comprising a screw member having a head and a shaft, the rod receiving elements of the first and second surgical screw devices being comprised of a hook sized to engage a fastening device.

25. The cross-connecting apparatus of claim 24 wherein the head of the screw member of the first and second surgical screw devices has an aperture that is hexagon-shaped.

26. The system of claim 25 wherein said undersurface of said head and said shaft of said screw member comprise threaded portions.

27. A method of securing at least two implantation rods, comprising:

provifing a cross-connecting apparatus comprising a first element having opposing ends, one end having at least one aperture, said other end of said first element having a recessed surface, said recessed surface including a central bore; a second element having opposing ends, one end having at least one aperture, said other end of said second element having a recessed surface, said recessed surface including an elongated aperture, said recessed surface of said second element being positioned to overlap said recessed surface of said first element; an adjustable tightening device positioned through said elongated aperture of said second element and within said central bore of said first element to secure said second element onto said first element, said tightening device being designed to rotatably fit and slidably move within said elongated aperture of said second element; and at least two rotatable hooking elements each comprising a hook and an adjustable securing device, each of said hooking devices being inserted within said apertures of said first and second elements;

attaching said hooks of said hooking elements onto the rods and securing said hooks using said adjustable securing device;

adjusting the distance between said first and second hooks by sliding said tightening device along said elongated aperture of said second element to a predetermined position; and securing said first and second elements to said predetermined position using said tightening device.

28. The method of claim 27 wherein said central bore of said recessed surface of said first element includes a protruding member and designing said protruding member to rotatably fit and slidably move within said elongated aperture of said second element.

29. A method of attaching a surgical screw onto a bone and securing at least two implantation rods comprising:

providing a cross-connecting surgical screw system comprising a first element having opposing ends, one end having a first surgical screw device, said other end of said first element having a recessed surface, said recessed surface including a central bore; a second element having opposing ends, one end having a second surgical screw device, said other end of said second element having a recessed surface, said recessed surface including an elongated aperture, said recessed surface of said second element being positioned to overlap said recessed surface of said first element; an adjustable tightening device positioned through said elongated aperture of said second element and within said central bore of said first element to secure said second element onto said first element, said tightening device being designed to rotatably fit and slidably move within said elongated aperture of said second element; and each of said first and second surgical screw devices comprises a screw member at one end, a rod receiving element at the other end and a locking device, attaching surgical screws to a host bone, affixing at least two implantation rods by joining together the implantations rods, the surgical screws and a cross-connecting surgical screw system.

30. The method of claim 29 wherein each of the first and second surgical screw devices further comprises a screw member having a head and a shaft, said head of said screw member having a spherical undersurface and a conical tapered recess; a receiver member having upper and lower portions, a u-shaped rod receiving channel, and an axial bore, said u-shaped channel having two lateral legs at said upper portion of said receiver member and forming an opening leading to said axial bore; said axial bore near said lower portion of said receiver member including an inwardly conical tapered surface, said conical surface having a diameter larger than said shaft of said screw member and a diameter smaller than said head of said screw member, said conical surface forming a support upon which said spherical undersurface of said head of said screw member rests when said screw member is guided through said bore to said lower portion of said receiver member; a pressure cap positioned within said axial bore of said receiver member and situated upon said head of said screw member, said pressure cap having upper and lower ends, said upper end of said cap comprising a concave radial portion upon which the rod is positioned, said lower end comprising a spherical portion situated upon said conical tapered recess of said head of said screw member; and said locking device for securing the rod within said u-shaped channel of said receiving member by applying a tightening torque upon the rod when positioned within said opening and said bore near said upper portion of said receiving member.

31. A surgical cross-connecting apparatus, comprising a first element having opposing ends, one end having at least one aperture, said other end of said first element having a protrusion;

a second element having opposing ends, one end having at least one aperture, said other end of said second element having a protrusion receiving element; said protrusion of said first element being designed to fit within said protrusion receiving element of said second element; and at least two rotatable hooking elements comprising a hook and an adjustable securing device, each of said hooking elements being inserted within said aperture of said first and second elements.

32. The surgical cross-connecting apparatus of claim 31 wherein said protrusion is bendable such that upon the insertion of said protrusion into said protrusion receiving element, said first and second elements form an angle during installment of said apparatus onto a patient.

33. The surgical cross-connecting apparatus of claim 32 wherein said protrusion is bent prior to insertion of said protrusion into said protrusion receiving element.

34. The surgical cross-connecting apparatus of claim 32 wherein said protrusion is bent after insertion of said protrusion into said protrusion receiving element.

35. The surgical cross-connecting apparatus of claim 31 further comprises a securing device and wherein said protrusion receiving member of said second element includes an aperture for receiving said securing device.

36. The surgical cross-connecting apparatus of claim 35 wherein said securing device is a set screw.

37. The surgical cross-connecting apparatus of claim 35 Wherein said protrusion comprises an aperture corresponding to said aperture of said protrusion receiving element, for receiving said securing device.

38. The surgical cross-connecting apparatus of claim 35 wherein said protrusion of said first element has a flat top surface for contacting said securing device.

39. The surgical cross-connecting apparatus of claim 31 wherein said protrusion receiving element comprises a central bore for securing said protrusion.

40. The surgical cross-connecting apparatus of claim 31 wherein said protrusion receiving element is designed to be bent during the installation process.

* * * * *